(12) United States Patent
Jahns et al.

(10) Patent No.: US 6,887,238 B2
(45) Date of Patent: *May 3, 2005

(54) SUCTION STABILIZED EPICARDIAL ABLATION DEVICES

(75) Inventors: Scott E. Jahns, Hudson, WI (US); Greg P. Werness, South St. Paul, MN (US); Jon M. Ocel, New Brighton, MN (US); David Lipson, North Andover, MA (US); Donald N. Jensen, Derwood, MD (US); David E. Francischelli, Anoka, MN (US); James R. Keogh, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/375,612

(22) Filed: Feb. 27, 2003

(65) Prior Publication Data

US 2003/0167056 A1 Sep. 4, 2003

Related U.S. Application Data

(63) Continuation of application No. 09/843,897, filed on Apr. 26, 2001, now Pat. No. 6,558,382, which is a continuation-in-part of application No. 09/558,976, filed on Apr. 27, 2000, now Pat. No. 6,514,250.

(51) Int. Cl.[7] .............................................. A61B 18/18
(52) U.S. Cl. ......................... 606/41; 607/101; 607/122
(58) Field of Search ........................ 606/41, 42, 45–50; 607/101–102, 119, 122, 126–128; 601/6, 7; 600/387

(56) References Cited

U.S. PATENT DOCUMENTS

| 5,405,376 A | 4/1995 | Mulier et al. |
| 5,452,733 A | 9/1995 | Sterman et al. |

(Continued)

FOREIGN PATENT DOCUMENTS

| WO | WO 01/05306 | 1/2001 |
| WO | WO 01/58373 | 8/2001 |

OTHER PUBLICATIONS

Grundeman, P. F., Experimental videothoracoscopic cannulation of the left atrial appendix: a feasible rapid approach for initiating left heart bypass? 1993, vol. 7; No. 6, Pagination 511, Journal—*Surgical Endoscopy*.

Thomas, Stuart P. et al., Mechanism, Localization and Cure of Atrial Arrhythmias Occurring After A New Intraoperative Endocardial Radiofrequency Ablation Procedure for Atrial Fibrillation, Nov. 2, 2000, vol. 35, *Journal of the American College of Cardiology*.

An article entitled "Radiofrequency Ablation of Cardiac Arrhythmias" (Lawrence S. Klein and William M. Miles, Scientific American Science & Medicine May/Jun. 1994, pp. 48–57.

(Continued)

Primary Examiner—Michael Peffley
(74) Attorney, Agent, or Firm—Thomas G. Berry; Jeffrey J. Hohenshell

(57) ABSTRACT

A suction assisted ablation device having a support surface, suction elements disposed adjacent the support surface, at least one electrode and at least one suction conduit is provided. The device may further include fluid openings, which allow fluid to irrigate target tissue and aid in ablation. A method for ablating tissue using suction is also provided.

71 Claims, 9 Drawing Sheets

U.S. PATENT DOCUMENTS

| | | | |
|---|---|---|---|
| 5,487,757 A | 1/1996 | Truckai et al. | |
| 5,540,681 A | 7/1996 | Strul et al. | |
| 5,545,200 A | 8/1996 | West et al. | |
| 5,571,088 A | 11/1996 | Lennox et al. | |
| 5,571,215 A | 11/1996 | Sterman et al. | |
| 5,573,533 A | 11/1996 | Strul | |
| 5,588,432 A | 12/1996 | Crowley | |
| 5,643,197 A | 7/1997 | Brucker et al. | |
| 5,725,524 A | 3/1998 | Mulier et al. | |
| 5,755,760 A | 5/1998 | Maguire et al. | |
| 5,779,699 A | 7/1998 | Lipson | |
| 5,797,960 A | 8/1998 | Stevens et al. | |
| 5,807,395 A | 9/1998 | Mulier et al. | |
| 5,823,955 A | 10/1998 | Kuck et al. | |
| 5,836,311 A * | 11/1998 | Borst et al. | 128/897 |
| 5,840,031 A | 11/1998 | Crowley | |
| 5,876,398 A | 3/1999 | Mulier et al. | |
| 5,913,854 A | 6/1999 | Maguire et al. | |
| 5,916,213 A | 6/1999 | Haissaguerre et al. | |
| 5,916,214 A | 6/1999 | Cosio et al. | |
| 5,919,188 A | 7/1999 | Shearon et al. | |
| 5,931,810 A | 8/1999 | Grabek | |
| 5,971,983 A * | 10/1999 | Lesh | 606/41 |
| 6,002,955 A | 12/1999 | Willems et al. | |
| 6,004,269 A | 12/1999 | Crowley et al. | |
| 6,016,809 A | 1/2000 | Mulier et al. | |
| 6,019,722 A | 2/2000 | Spence et al. | |
| 6,051,008 A | 4/2000 | Saadat et al. | |
| 6,063,081 A | 5/2000 | Mulier et al. | |
| 6,068,629 A | 5/2000 | Haissaguerre et al. | |
| 6,086,583 A | 7/2000 | Ouchi | |
| 6,159,207 A | 12/2000 | Yoon | |
| 6,159,208 A | 12/2000 | Hovda et al. | |
| 6,161,543 A | 12/2000 | Cox et al. | |
| 6,162,195 A | 12/2000 | Igo et al. | |
| 6,165,174 A | 12/2000 | Jacobs et al. | |
| 6,183,469 B1 | 2/2001 | Thapliyal et al. | |
| 6,190,353 B1 | 2/2001 | Makower et al. | |
| 6,190,381 B1 | 2/2001 | Olsen et al. | |
| 6,231,518 B1 | 5/2001 | Grabek et al. | |
| 6,237,605 B1 | 5/2001 | Vaska et al. | |
| 6,311,692 B1 * | 11/2001 | Vaska et al. | 128/898 |
| 6,425,912 B1 | 7/2002 | Knowlton | |
| 6,514,249 B1 * | 2/2003 | Maguire et al. | 606/41 |
| 6,558,382 B2 | 5/2003 | Jahns et al. | |
| 6,652,518 B2 * | 11/2003 | Wellman et al. | 606/41 |
| 6,663,622 B1 * | 12/2003 | Foley et al. | 606/34 |
| 2002/0002372 A1 | 1/2002 | Jahns et al. | |
| 2003/0078575 A1 | 4/2003 | Jahns et al. | |

OTHER PUBLICATIONS

An article entitled "Physiology of the Heart" Conduction System (A, Unit Four Transportation, pp. 472–479??).

An article entitled "Transcatheter Radiofrequency Ablation of Atrial Tissue Using a Suction Catheter" (Th Lavergne, L. Pruner, L. Cuize, P. Bruneval, *D, Von Euw, J–Y. Le Heuzey and P. Peronneau, (From the Inserm U 256 & 28 (*), Paris, France.) PACE, vol. 12, Jan. 1989, Part II, pp. 177–186).

An article entitled "Radiofrequency Ablation of Atrial Fibrillation in Patients undergoing concomitant Cardiac Surgery. First Experience" ( Willem P. Beukema, MD, Hauw T. Sie, MD, Anand R. Ramdat Misier, MD, Max MP Haalebos, MD, Cor W. Schipper, Hospital De Weezenlanden, Zwolle, The Netherlands; PACE Apr. 1997: 20 (Part II), P. 1100 (abstract only).

An article entitled "Efficacy of a Simple Left Atrial Procedure for Chronic Atrial Fibrillation In Mitral Valve Operations," (Taijiro Sueda, MD, al., Haidyuki Nagata, MD, Kazumasa Orihashi, MD, Satoru Moria, MD, Kenji Okada, MD, Masafumi Sueshiro, MD, Shinji Hirai, MD, and Yuichiro Matsuura, MD, First Department of Surgery, Hiroshima University, School of Medicine, Hiroshima, Japan, © 1997 by the Society of Thoracic Surgeons, pp. 1070–1075; Ann Thoracic Surg 1997; 63: 1075).

An article entitled "Minimally Invasive Endocardial and Epicardial Maze Procedure" (The Pennsylvania State University, Milton S. Hershey Medical Center, Hershey, Pennsylvania, Revised: Nov. 25, 1998, pp. 1–25).

Abstracts From the 70th Scientific Sessions entitled "Early Results of Cox–Maze Procedure Combined with Mitral Valve Repair"(Nobuhiro Hand, Hartzell V. Schaff, Betty J. Anderson, Stephen L. Kopecka, Mayo Clinic, Rochester, MN Circulation, 1997; 96 (8, Suppl): p. 1–731) (abstract only).

* cited by examiner

SUCTION STABILIZED EPICARDIAL ABLATION DEVICES

CROSS-REFERENCE TO RELATED APPLICATION

This application is a continuation of U.S. patent application Ser. No.: 09/843,897, filed on Apr. 26, 2001, now U.S. Pat. No. 6,558,382, which is a continuation-in-part of U.S. patent application Ser. No.: 09/558,976, filed on Apr. 27, 2000, now U.S. Pat. No. 6,514,250.

FIELD OF THE INVENTION

This invention relates to ablation devices that are used to create lesions in tissue. More particularly, this invention relates to ablation devices that use vacuum or suction force to hold the tissue in a manner that creates [linear] lesions. This invention also relates to diagnostic devices that are used to monitor or evaluate a physiological process. More particularly, this invention relates to diagnostic devices that use vacuum or suction force to hold the device against tissue.

BACKGROUND OF THE INVENTION

The action of the heart is known to depend on electrical signals within the heart tissue. Occasionally, these electrical signals do not function properly. The maze procedure is a surgical operation for patients with atrial fibrillation that is resistant to medical treatment. In this procedure, incisions are created in the right and left atria to produce an orderly passage of the electrical impulse from the SA node to the atrioventricular node. Blind passageways are also created to suppress reentry cycles. Currently, the lesions may still be created using a traditional cut and sew technique. The scar tissue resulting from the procedure results in a non-conductive lesion.

Ablation of cardiac conduction pathways in the region of tissue where the signals are malfunctioning has been found to eliminate such faulty signals. Ablation is also used therapeutically with other organ tissue, such as the lungs, liver, prostate and uterus. Ablation may also be used in treatment of disorders such as tumors, cancers or undesirable growth.

Currently, electrophysiology (EP) ablation devices generally have one or more electrodes at their tips. These devices may be used for both diagnosis and therapy. In one instance, electrodes at the tips of EP ablation devices allow the physician to measure electrical signals along the surface of the heart. This is called mapping. When necessary, in another instance, the physician can also ablate certain tissues using, typically, radio frequency (RF) energy conducted to one or more ablation electrodes or the physician can ablate certain tissues using methods such as microwave, laser, ultrasound or cryo.

Sometimes ablation is necessary only at discrete positions along the tissue. This is the case, for example, when ablating accessory pathways, such as in Wolff-Parkinson-White syndrome or AV nodal reentrant tachycardias. At other times, however, ablation is desired along a line, called linear ablation. This is the case for atrial fibrillation, where the aim is to reduce the total mass of electrically connected atrial tissue below a threshold believed to be critical for sustaining multiple reentry wavelets. Linear lesions are created between electrically non-conductive anatomic landmarks to reduce the contiguous atrial mass.

Linear ablation is currently accomplished in one of several ways. One way is to position the tip portion of the ablation device so that an ablation electrode is located at one end of the target site. Then energy is applied to the electrode to ablate the tissue adjacent to the electrode. The tip portion of the electrode is then slid along the tissue to a new position and then the ablation process is repeated. This is sometimes referred to as the burn-drag-burn technique. This technique is time-consuming (which is not good for the patient) and requires multiple accurate placements of the electrode (which may be difficult for the physician). Furthermore, even if the ablation process creates a continuously linear line along the top surface of the target tissue, it is not assured that the tissue is continuously and completely ablated through further layers of the target tissue (i.e. it is not assured that transmurality is achieved).

A second way of accomplishing linear ablation is to use an ablation device having a series of spaced-apart band or coil electrodes which, after the electrode portion of the ablation device has been properly positioned, are energized simultaneously or one at a time to create the desired lesion. If the electrodes are close enough together the lesions run together sufficiently to create a continuous linear lesion. While this technique eliminates some of the problems associated with the burn-drag-burn or "spot burn" technique, some repositioning of the ablation device may be required to create an adequately long lesion. In addition, it may be difficult to obtain adequate tissue contact pressure for each electrode in a multi-electrode ablation device. Also, the use of multiple electrodes to create the linear lesion tends to make the tip portion more expensive to make, more bulky and may cause the tip portion to be stiffer than with a single electrode.

Another ablation-related problem results from the delivery of RF energy to muscular tissue, such as the heart. Ablation of such tissue using conventional ablation devices has a tendency to char or burn the blood or tissue with which the electrodes are in contact if the temperatures exceed a certain threshold (for example, greater than 50° C.). This increases the difficulty of the ablation process because it is necessary to clean the tip portion after a series of burns. Moreover, overheating the tissue in the vicinity of the target site can desiccate the tissue and can cause overburning.

It would be desirable to have an ablation device which is easy to position in relation to the target tissue and which stays stable in position in relation to the target tissue.

It would further be desirable to have an ablation device which, when positioned, is capable of easily creating a linear, transmural lesion.

It would further be desirable to have an ablation device that is able to monitor tissue temperature in order to avoid burning the tissue.

It would further be desirable to provide a means for monitoring one or more chemical, physical or physiological characteristics of a bodily tissue or fluid during the ablation procedure.

It would further be desirable to provide a system and method for controllably monitoring and ablating.

SUMMARY OF THE INVENTION

One aspect of the present invention provides a suction assisted ablation device. The device includes a support surface, having a first and a second face, a plurality of suction elements disposed adjacent the support surface on the first face, at least one conductive element disposed adjacent the support surface on the first face; and at least one suction conduit operatively connected with the suction elements. The device may also include a maneuvering apparatus, such as a pull wire assembly. The device may also include at least one thermocouple element. The device may include one conductive element on a first support surface and a separate conductive element on a second support surface. The conductive element may be a plurality of needle electrodes. The device may also include at least one fluid opening, which may be located within the conductive element. The conductive element may also be made of a material capable of releasing fluid.

Another aspect of the invention provides a method of ablating tissue. A suction assisted ablation device comprising a support surface, having a first and a second face, a plurality of suction elements disposed adjacent the support surface on the first face, and at least one conductive element disposed adjacent the support surface on the first face is provided. The first face of the device is placed adjacent an area of tissue. Suction is conducted to the suction elements via the suction conduit. The tissue is grasped with the suction and ablated. At least one fluid outlet may be provided adjacent the support surface and fluid may be released via the fluid outlet. The fluid outlet may be located within the conductive element. The device may be placed using a maneuvering apparatus. At least one thermocouple element may be placed in communication with at least one suction element and a thermal environment of the suction element may be measured using the thermocouple element. The tissue may be ablated until the measurement of the thermal environment reaches a given level. A second support surface having a second conductive element disposed adjacent a first face of the second support surface may also be provided. The first face of the second support surface may be placed in line with the first support surface to complete a circuit. The tissue is ablated.

Another aspect of the invention provides a tissue ablation system. The system comprises at least two support surfaces, each support surface having a first and a second face, a plurality of suction elements disposed adjacent the support surface on the first face, at least one conductive element disposed adjacent the support surface on the first face, at least one suction conduit operatively connected with the suction elements, and at least one maneuvering apparatus, such as a pull wire assembly. The support surfaces may be disposed consecutively to each other in a linear manner along the maneuvering apparatus so that a continuous ablation lesion is achieved. The system may also include a fluid delivery system, which may incorporate at least one fluid opening disposed adjacent the support surface, a fluid conduit, a conductive element including fluid openings or a conductive element made of a material that releases fluid.

Another aspect of the invention provides a method of mapping the heart. A suction assisted ablation device comprising a support surface, having a first and a second face, a plurality of suction elements disposed adjacent the support surface on the first face, at least one electrode disposed adjacent the support surface on the first face and at least one suction conduit operatively connected with the suction elements is provided. The first face of the device is placed adjacent an area of tissue. Suction is conducted to the suction elements via the suction conduit. The tissue is grasped with the suction. A signal is sent through a first electrode. The signal is received through a second electrode. The distance is mapped based on the signal from the first electrode to the second electrode.

Another aspect of the invention provides a method of pacing a heart. A suction assisted ablation device comprising a support surface, having a first and a second face, a plurality of suction elements disposed adjacent the support surface on the first face, at least one electrode disposed adjacent the support surface on the first face and at least one suction conduit operatively connected with the suction elements. The first face of the device is placed adjacent an area of tissue. Suction is conducted to the suction elements via the suction conduit. The tissue is grasped with the suction. Electrical impulses are sent through the electrode at regular interval and the heart is paced to beat with the impulses.

Another aspect of the invention provides a method of ablating tissue. A suction assisted ablation device comprising a support surface, having a first and a second face, a plurality of suction elements disposed adjacent the support surface on the first face, at least one needle electrode disposed adjacent the support surface on the first face and at least one suction conduit operatively connected with the suction elements. The first face of the device is placed adjacent an area of tissue. The tissue is penetrated with the needle electrode. Suction is conducted to the suction elements via the suction conduit. The tissue is grasped with the suction; and ablated.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
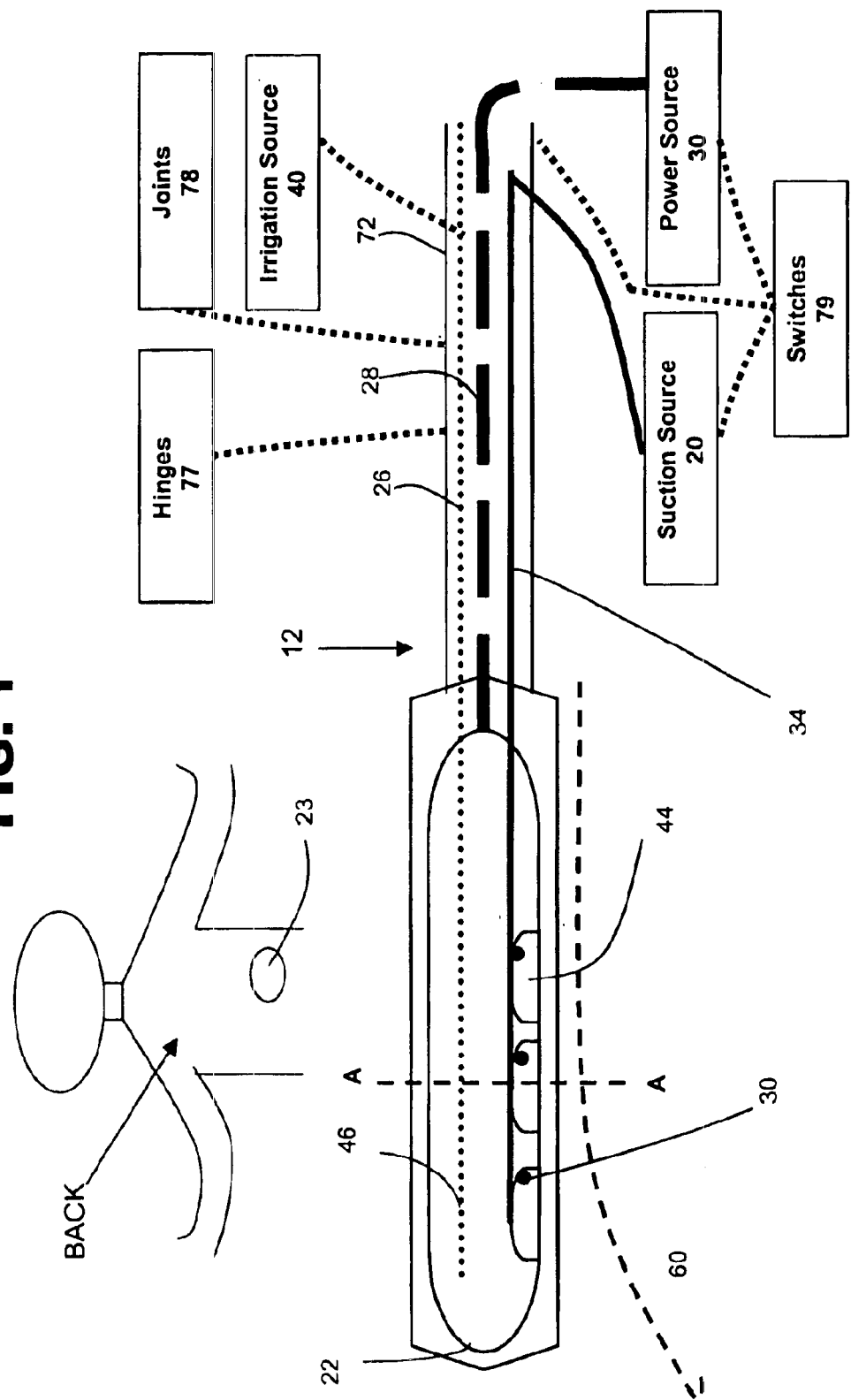
FIG. 1 is a side view of the suction assisted ablation device in accordance with the present invention shown within a system for ablating tissue.

FIG. 1 shows one embodiment of system 10 for ablating tissue, such as organic tissue, in accordance with the present invention. Typically the tissue to be ablated will be located within the body cavity, such as the endocardial or epicardial tissue of the heart. Other body organ tissue, such as the liver, lungs or kidney, may also be ablated using the present invention. Tissue types that may be ablated include skin, muscle or even cancerous tissue or abnormal tissue growth.

System 10 may include an ablation device 12 that comprises at least one conductive element 22, such as an electrode, and a connection 28 to a power source 30. Ablation device 12 may also include one or more suction elements 44 and a suction conduit 34 that provides suction from a suction source 20. System 10 also may include a conduit 26 to an irrigation source 40 that provides irrigation fluid to the ablation site. System 10 may also include temperature-sensitive elements 36, which may have the same power source 30 as the electrodes or may have their own power source.

System 10 may also include an indifferent (non-ablating) electrode 23 which may serve as a return plate for energy transmitted through electrode 22. Electrode 23 may be placed elsewhere on the patient's body other than the ablation site. For example, electrode 23 may be placed on the patient's back, thigh or shoulder.

Ablation device 12 may be any suitable ablation tool using suction to anchor the ablation device to tissue being ablated, such as, for example, a catheter, an electrocautery device, an electrosurgical device, a suction-assisted ablation tool, an ablation pod, an ablation paddle, an ablation hemostat or an ablation wire. Ablation device 12 and its components are preferably made of a biocompatible material such as stainless steel, biocompatible epoxy or biocompatible plastic. Preferably, a biocompatible material prompts little allergenic response from the patient's body and is resistant to corrosion from being placed within the patient's body. Furthermore, the biocompatible material preferably does not cause any additional stress to the patient's body, for example, it does not scrape detrimentally against any elements within the surgical cavity. Alternatively, the biocompatibility of a material may be enhanced by coating the material with a biocompatible coating.

Preferably, ablation device 12 may be permanently or removably attached to or incorporate a maneuvering apparatus for manipulating device 12 onto a tissue surface. For example, ablation device 12 may be attached to a handle 72 such as shown in FIG. 1. Ablation device 12 may also be located on one or more of the jaws of a hemostat-like device. Ablation device 12 may also be used in conjunction with a traditional catheter, for example, in a closed heart ablation procedure. Ablation device 12 may also be maneuvered with a leash or pull-wire assembly. Ablation device may also be positioned on a pen-like maneuvering apparatus such as the Sprinkler pen available from Medtronic, Inc. Alternatively any appropriate flexible, malleable or rigid handle could be used as a maneuvering apparatus. Alternatively, any appropriate endoscopic or thoroscopic-maneuvering apparatus may also be used with device 12.

Device 12 also preferably includes a connection 28 suitable for conducting energy to device 12, particularly to conductive element 22 from a power source.

The conductive element 22 of ablation device 12 may preferably be an electrode. This electrode 22 may be positioned in any suitable place on device 12. Preferably electrode 22 is placed near an end of the device 12, away from the user, to be more easily manipulated against the tissue 60 to be ablated.

Figure 2:
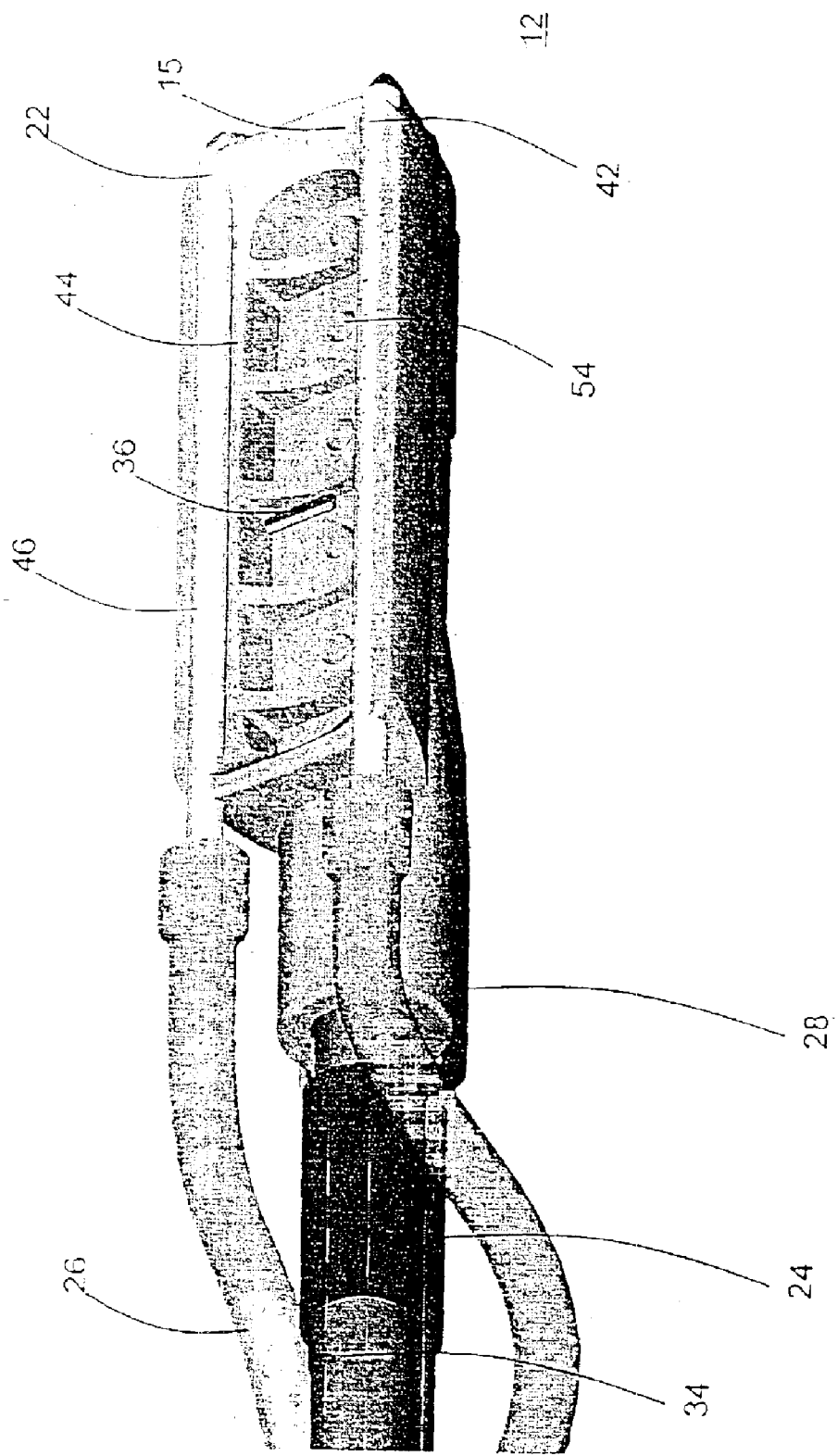
FIG. 2 is a bottom view of one embodiment of the suction assisted ablation device of the present invention, showing a first configuration of the suction elements and of the ablation electrodes.

FIG. 2 shows one embodiment of a device 12 for ablating organic tissue in accordance with system 10 of the present invention. Suction assisted ablation device 12 may comprise at least one face 15 that may conform to the surface of the target tissue 60. The face 15 may be any configuration that conforms to the surface of the target tissue, such as the slightly curved or arcuate configuration of FIG. 1. Suction device 12 may also include a suction conduit 34 that may be connected to least one suction port 44 containing a suction opening 54. Suction device may also have at least one conductive element 22 disposed adjacent face 15. For example, two conductive elements 22, 42 are shown in FIG. 2. Preferably, the conductive element 22, 42 may be an electrode. Alternatively, suction device 12 may be made of a conductive polymer and may serve as a conductive element. The distal end of device 12 may be positioned near the ablation site and the proximal end may be positioned towards the surgeon.

Preferably, when face 15 of suction device 12 is positioned against the target tissue, face 15 is adapted to conform to the surface of the tissue. This may be accomplished by making suction device 12 from a flexible material, such as, for example, a pliable polymer, biocompatible rubber, thermoplastic elastomer or PVC. Alternatively, suction device 12 may be made of a more rigid material covered with an elastic over face 15. Suction force being applied through device 12 may cause device 12 to conform more closely to the shape of the target tissue. Device 12 may also be made of a malleable stainless steel or other material that is shapeable but not necessary flexible. Device 12 may also be made of a conductive polymer.

Ablation device 12 may also be permanently or removably attached to a suction tube 24. Suction conduit 34 may be located within tube 24. Conduit 34 may communicate suction to the target tissue surface via the suction openings 54 of suction ports 44 in device 12.

The suction ports 44 may be arranged three to six ports in a row, although the specific number of ports and their position may vary. Preferably, for a linear lesion to result from the ablation process, the ports are arranged linearly. Device 12 may be covered with a covering during insertion to prevent blood or tissue from clogging the ports 44, although this is not necessary. Such coverings may include coverings of biocompatible material that would cover device 12. Alternatively, coverings may be placed over ports 44, such as, for example, mesh coverings or ribbed coverings.

Each suction port 44 has a suction opening 54, which may be located in the center or at a position slightly off-center of suction port 44. Although the openings 54 are circular in FIG. 2, other shapes may be used. The suction ports 44 may also be any suitable shape. For example, in the embodiment of FIG. 2, the ports 44 are rectangular. Additionally, suction openings 54 may be covered with a covering such as described above to prevent blood or tissue from clogging the openings 54.

Preferably, each suction opening 54 has a smaller diameter than the area of suction port 44. This creates a high resistance pathway between suction port 44 and suction conduit 34. Because of this, loss of a tissue-to-port seal in one suction port (and thus loss of fixation of the suction port to the tissue) should not cause a precipitous pressure drop in the remainder of the suction ports.

Ablation device 12 may be permanently or removably attached to at least one connection 28 for conveying energy to electrodes 22, 42 from power source 30. This energy is typically electrical, such as radiofrequency (RF) energy. However, it may also be any appropriate type of energy such as, for example, microwave or ultrasound energy. Preferably, electrode 22 runs the length of one side of device 12 and electrode 42 runs the length of the opposite side of device 12. Electrode 22 may be maneuvered into contact with the target tissue to ablate the tissue. In the embodiment of FIG. 2, two electrodes are shown in a bipolar arrangement. In such a bipolar arrangement, electrode 42 may also be maneuvered into contact with target tissue 60 to ablate the tissue.

Ablation device 12 may be permanently or removably attached to at least one fluid conduit 26 for irrigating the ablation site with a fluid. Alternatively, ablation site may not be irrigated. Fluid is conveyed to the site via fluid openings 46 which are preferably integrated into electrodes 22, 42. However, fluid may be delivered to the site via a separate irrigation mechanism, such as an irrigation pump (not shown). Moreover, fluid openings 46 may be disposed in any appropriate manner on device 12.

Suction ablation device 12 may be colored so that it can be easily visible against the target tissue. Alternatively, it may be clear to provide less distraction to the surgeon or to provide viewing of blood or other material being suctioned. Suction tube 24 may be a flexible tube constructed of a soft plastic which could be clear or colored. Suction ports 44 may be constructed of biocompatible rubber or epoxy, which could be clear or colored.

Electrodes 22, 42 may be constructed of stainless steel, platinum, other alloys, or a conductive polymer. If device 12 is made of a more flexible material, electrodes 22, 42 may be made of materials that would flex with the device 12. Such flexible electrodes may be, for example, made in a coil or spring configuration. Flexible electrodes 22, 42 may also be made from a gel, such as a hydrogel. Furthermore, electrodes 22, 42 may also be an electrode designed to deliver fluid, such as, for example, a microporous electrode, a "weeping" electrode, or an electrode made of a hydrogel.

A source 20 for creating suction may be attached to suction tube 24 at the proximal end, preferably by a standard connector. This suction source 20 may be the standard suction available in the operating room and may be coupled to the device 12 with a buffer flask (not shown). Suction is provided at a negative pressure of between 200–600 mm Hg with 400 mm Hg preferred.

System 10 may include at least one temperature-sensitive element 36. The temperature-sensitive element 36 is positioned to communicate with at least one of suction ports 44. Preferably, an element 36 is positioned to communicate with each suction port 44. These elements may be, for example, thermocouple wires, thermisters or thermochromatic inks. These thermocouple elements allow temperature to be measured. Such monitoring of temperature may be crucial. Too high a temperature will char the tissue or cause the blood at the ablation site to coagulate. Preferably, the elements 36 may be adhered within suction ports 44 so as to contact the tissue when it is suctioned into the ports. Thermocouple elements that may be used are 30 gauge type T thermocouple wire from Dodge Phelps Company. One type of conductive epoxy which may be used to adhere the elements is epoxy no. BA-2902, available from Trecon.

A separate temperature sensitive element 36 may be adhered or mounted within each suction port 44. Alternatively, a temperature sensitive element may be incorporated to run through all of the suctions ports 44.

As ablation occurs, it is sometimes desirable to irrigate the ablation site with irrigation fluid, which may be, for example, any suitable fluid such as saline, an ionic fluid that is conductive or another conductive fluid. The irrigating fluid may cool the electrode 22 of ablation device 12. Irrigated ablation is also known to create deeper lesions that are more likely to be transmural. Transmurality is achieved when the full thickness of the target tissue is ablated. The application of fluid to an ablation site may also prevent electrodes, particularly metal electrodes, from contacting the target tissue. Direct contact of electrodes to the target tissue may char or burn the tissue, which may clog the device. Furthermore, continuous fluid flow may keep the ablation device surface temperature below the threshold for blood coagulation, which may also clog the device. Use of irrigating fluid may therefore reduce the need to remove a clogged ablation device for cleaning or replacement. The presence of an ionic fluid layer between electrode 22 and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as Lidocaine, $CA^{++}$ blockers, or gene therapy agents may also be delivered before, with or after the delivery of the irrigating fluid. Irrigation source 40 may be any suitable source of irrigation fluid such as, for example, a standard irrigation pump (not shown). This pump may also be connected to power source 30 or may have its own source of power. Preferably, device 12 also includes a conduit 26 for delivering irrigation to the ablation site from irrigation source 40.

In the embodiment of FIG. 1, fluid openings 46 may be located within the electrode 22 itself. These openings may be holes machined into the electrode 22. These openings may deliver fluid to the ablation site as described above. Furthermore, electrode 22 may also be an electrode designed to deliver fluid, such as, for example, a microporous electrode, a "weeping" electrode, an electrode made of a microporous polymer or an electrode made of a hydrogel.

Figure 3:
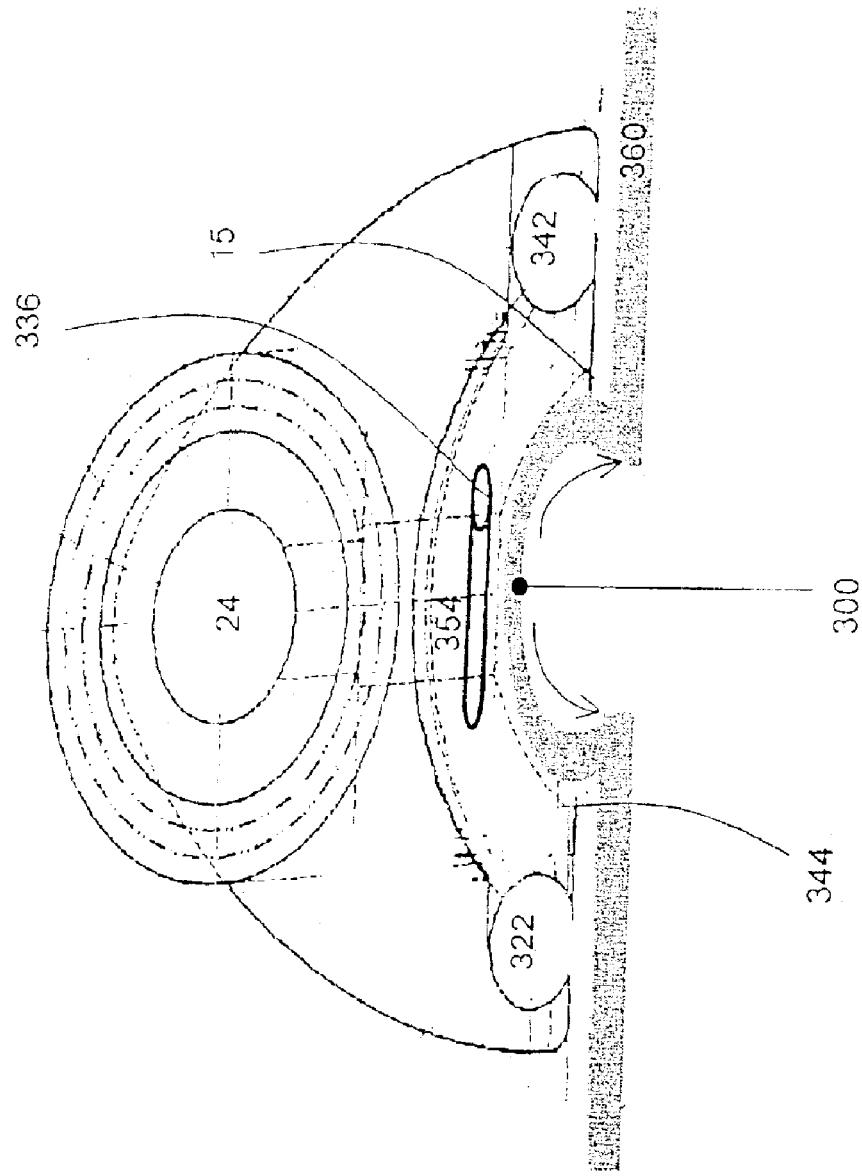
FIG. 3 is a cross-sectional view of one embodiment of the suction assisted ablation device of the present invention, showing suction activity and ablation pattern at one suction site.

Referring now to FIG. 3, a close-up cross section is shown, taken along line A—A of FIG. 1. In use, the embodiment of device 12 shown in FIGS. 1 and 2 is placed against target tissue 360 so that when a suction force is applied through openings 354, the target tissue is pulled into the suction port 344. Fluid flows from openings 46 towards the target tissue as indicated by the arrows. Openings 46 are preferably angled at about 30 degrees. Openings 46 preferably face towards suction ports 344. Ablation may begin at point 300 of the tissue and spread in the direction indicated by the dofted arrows. If left over time, the entire piece of tissue suctioned into the ports 344 may be ablated.

Electrodes 322, 342 are brought to a temperature sufficient to ablate the tissue within the ports 44. Thermocouple elements 336 may be used to monitor the temperature and when a given threshold temperature is reached, the surgeon may end ablation. This configuration of device 12 is especially useful because it gives an accurate measurement of the tissue temperature since the tissue 360 is in direct contact with the thermocouple elements 336 located near ports 344. Thus the temperature of the tissue may be measured by thermocouple elements rather than the temperature of the electrode 322 being measured. The temperature of the tissue may also be determined based on ablation time.

The resulting lesion may be transmural. If the tissue is allowed to heat until the elements 336 indicate a temperature that usually indicates cell death (such as, for example, 15 seconds at 55°), this may indicate that all the tissue has reached this temperature. In turn, this may indicate that the lesion is transmural.

The ablation resulting from the arrangement of electrodes in FIGS. 2 and 3 is linear. The width of the resulting ablation lesion may be determined by the space between electrodes 22, 42. The width of the resulting ablation lesion may also be determined by the depth of the suction port 44 and the amount of the tissue suctioned into port 44. The depth of the lesion may be controlled by the depth of the suction port 44 and the amount of suction force applied. The depth of the lesion may also be determined by the power applied to the conductive element and the length of ablation time. The lesion resulting from the suction port 344 of FIG. 3 will be repeated at each subsequent corresponding suction port along the length of device 12. It is contemplated that for a longer lesion, a longer pod could be used or a series of pods could be strung together. A single pod could also be used to create a longer lesion by ablating to create a first lesion and then being moved to create a second lesion in line with the first lesion.

Figure 4:
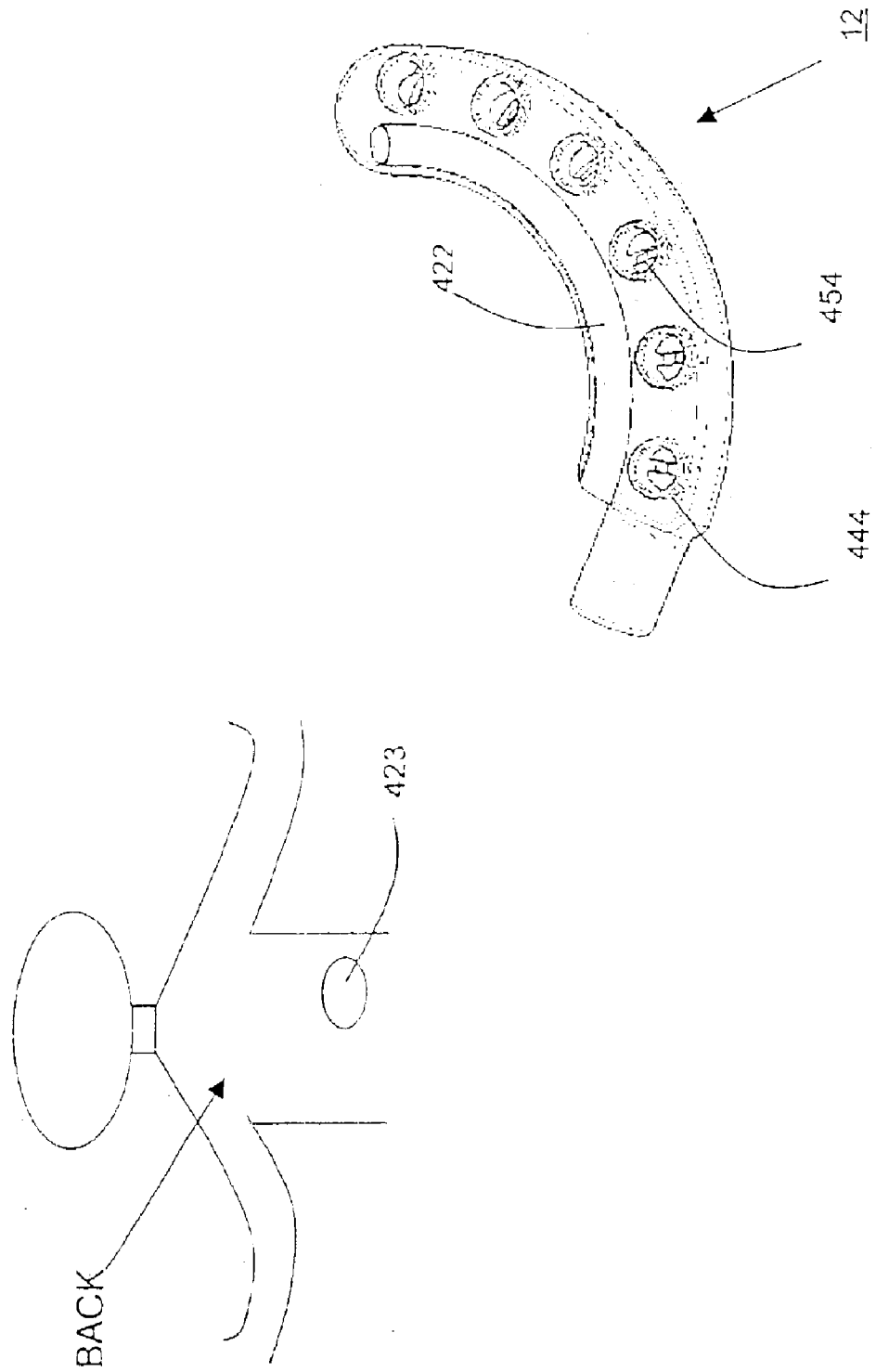
FIG. 4 is a bottom view of a second embodiment of the suction assisted ablation device of the present invention, showing a second configuration of the suction elements and of the ablation electrodes.

FIG. 4 shows another embodiment of the invention shown in FIG. 3. In this embodiment, electrodes 422, 423 are arranged in a unipolar arrangement. Electrode 422 is placed on the device 12 while another electrode 423 acts as a ground patch (indifferent, or non-ablating electrode) and is placed separately from the device 12. For example, electrode 422 on device 12 could be placed on a surface of the heart. Then corresponding electrode 423, which could be on a separate support surface, could be placed on the back of the patient to complete the circuit. Although the suction ports 444 may be arranged in a linear manner, ports 444 may be arranged in any other appropriate configuration, including for example, in an arcuate or radial arrangement. Although suction openings 454 may be circular, they may also be any appropriate shape to deliver suction. The lesions created by this sort of unipolar arrangement tend to be wider than those created by a bipolar arrangement.

In the unipolar arrangement of FIG. 4, suction ports 444 are used to grasp target tissue (not shown) but do not pull the tissue into the ports for ablating. Fluid would flow from openings in the electrode 423 or in device 12 in the same manner as described above. Ablation would occur in a similar manner to that described above although the device 12 remains uniformly on the surface of the target tissue rather than pulling the tissue into the ports for ablation.

Figure 5:
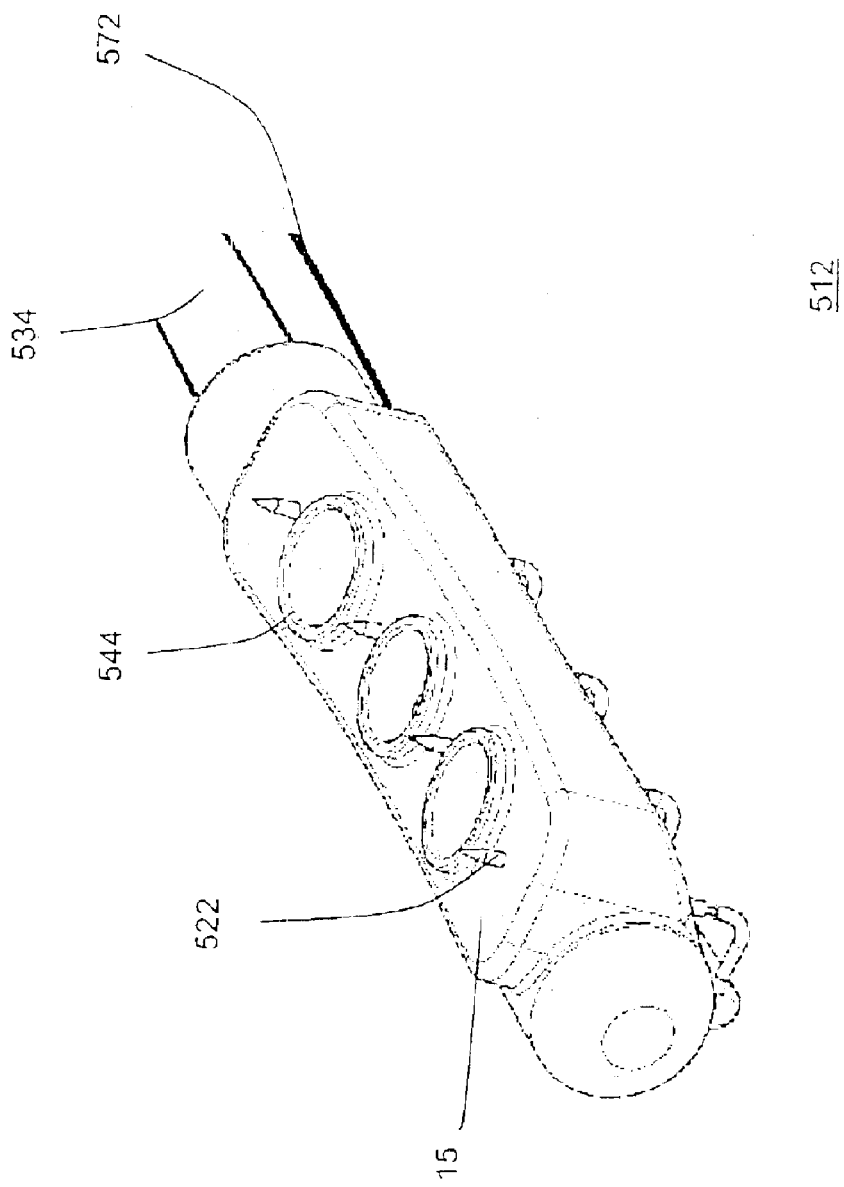
FIG. 5 is a bottom view of another embodiment of the suction assisted ablation device of the present invention.

It is contemplated that the electrodes used in the present invention could include any appropriate electrodes for performing ablation such as, for example, metal electrodes, braided metal electrodes or needle electrodes FIG. 5 shows another embodiment of the suction ablation device 512 of the present invention, in which the conductive element may be a series of needle electrodes 522. A unipolar arrangement of the electrodes 522 is shown. Alternatively, the electrodes may be arranged in a bipolar configuration similar to the arrangement of FIG. 2. In a bipolar arrangement, one series of needle electrodes may be arranged down the length of one side of the suction ports 544 and another series of electrodes 522 arranged down the length of the other side. Needle electrodes may be used to poke through fatty tissue covering the target tissue. They may then be used to poke into the target tissue. Suction may then be applied as described above to hold electrodes in place. Ablation may then occur as described above. Additionally, device 512 shows suction conduit 534 which may provide suction to ports 544 and pull wire 572 that serves as a maneuvering apparatus for device 512.

The device 12 may also be used in electrical mapping functions. For example, electrode 22 may be placed on one area of the heart and an appropriate signal sent through it. Then the electrode 42 may receive the signal from electrode 22. From the strength of the signal, the distance of electrode 22 from electrode 42 may be determined. Conduction delay or block can help determine transmurality of lesions.

Device 12 may also be used in pacing functions. For example, device 12 may grasp the heart as described above. Then energy may be sent through electrodes, 22, 42 at regular intervals. This energy may cause the heart to beat simultaneously to the signals sent through electrodes 22, 42. The device 12 may thus pace the heart at an appropriate beating rate, thereby serving as a pacemaker. This may be used, for example, during a surgical procedure when it might be necessary to regulate the heart's beating temporarily.

Figure 6:
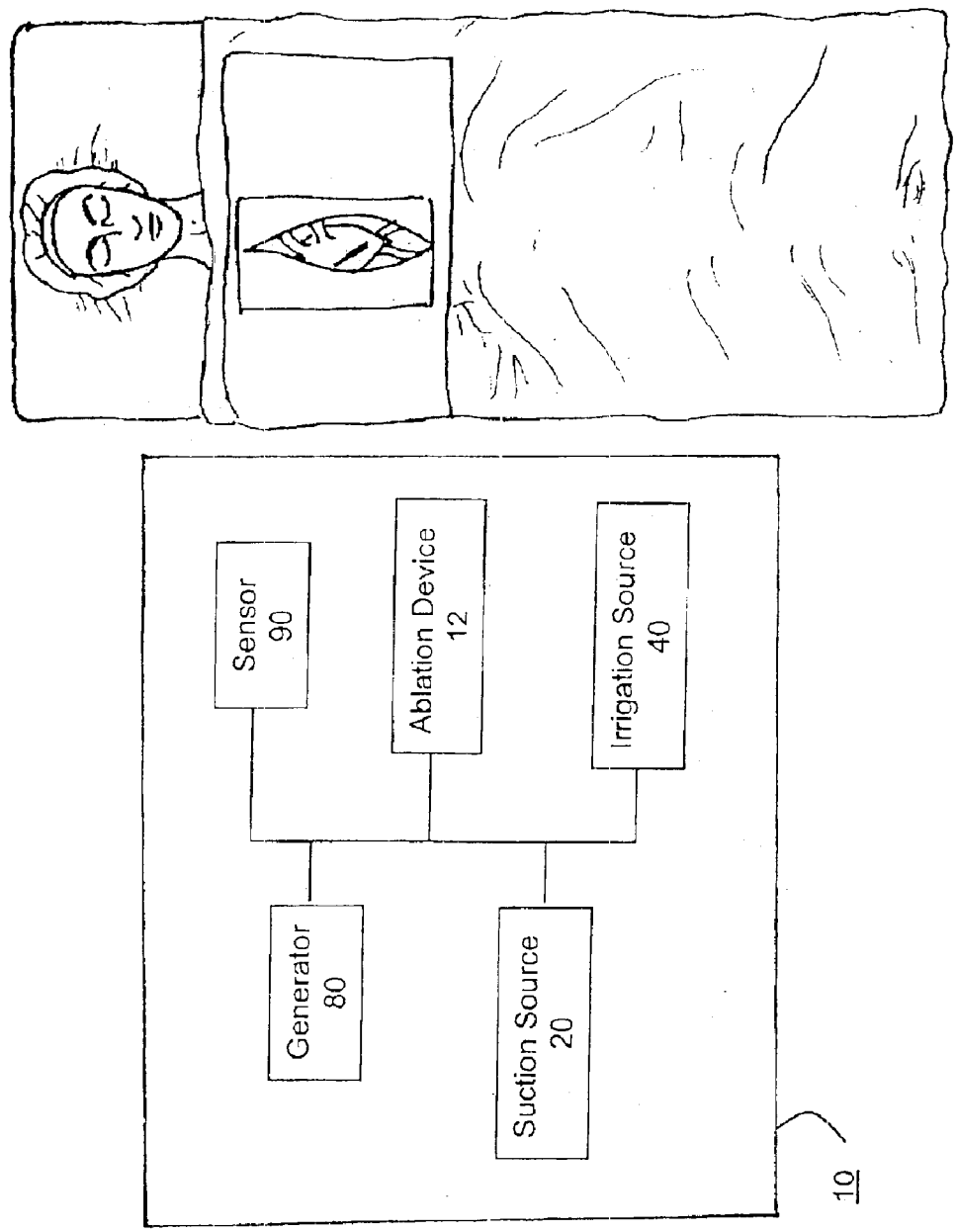
FIG. 6 is a schematic view of another embodiment of an ablation system for ablating tissue in accordance with the present invention.

FIG. 6 shows a schematic view of another embodiment of system 10 for ablating tissue in accordance with the present invention. In this embodiment, system 10 is shown to comprise ablation device 12, a suction source 20, an irrigation source 40, a generator 80, and a sensor 90. As mentioned earlier, system 10 may also include an indifferent (non-ablating) electrode 23 (not shown in FIG. 6). As shown in FIG. 1, the indifferent electrode 23 may be placed elsewhere on the patient's body such as the back, thigh or shoulder or another site other than the ablation site.

Ablation device 12 may comprise one or more energy transfer elements, one or more suction openings, a suction conduit that provides suction from suction source 20, and a conduit that provides irrigation fluid from irrigation source 40. Ablation device 12 may also comprise a connector for connecting ablation device 12 to generator 80.

As discussed above, ablation device 12 and its components are preferably made of a biocompatible material. Biocompatible materials or biomaterials are usually designed and constructed to be placed in or onto tissue of a patient's body or to contact fluid of a patient's body. Ideally, a biomaterial will not induce undesirable reactions in the body such as blood clotting, tumor formation, allergic reaction, foreign body reaction (rejection) or inflammatory reaction; will have the physical properties such as strength, elasticity, permeability and flexibility required to function for the intended purpose; may be purified, fabricated and sterilized easily; will substantially maintain its physical properties and function during the time that it remains in contact with tissues or fluids of the body.

Materials that are either biocompatible or may be modified to be biocompatible and may be used to make ablation device 12, sensor 90 and/or their components may include metals such as titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, rubber, minerals or ceramics such as hydroxapatite, epoxies, human or animal protein or tissue such as bone, skin, teeth, collagen, laminin, elastin or fibrin, organic materials such as wood, cellulose, or compressed carbon, and other materials such as glass, and the like. Materials that are not considered biocompatible may be modified to become biocompatible by a number of methods well known in the art. For example, coating a material with a biocompatible coating may enhance the biocompatibility of that material.

One or more surfaces of ablation device 12, sensor 90 and/or their components may be coated with one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand). Biological agents may be found in nature (naturally occurring) or may be chemically synthesized by a variety of methods well known in the art.

Ablation device 12 may comprise a maneuvering apparatus or means such as shaft or handle 72. Handle 72 may be rigid or flexible. Handle 72 may comprise one or more hinges 77 or joints 78 for maneuvering and placing conductive elements 22 and/or suction elements 44 against tissue. The hinges or joints of handle 72 may be actuated remotely, for example, from outside a patient's body. Handle 72 may be malleable or shapeable. Maneuvering means may be made of a shape memory alloy wherein heat may be use to change the shape of maneuvering means. Maneuvering means may be remotely steerable, for example, with pull wires. Maneuvering means may be a catheter.

Ablation device 12 may comprise a suction head having a tissue contact surface. The suction head may be flexible thereby allowing the head to conform to the surface of target tissue. The suction head may be malleable thereby allowing a surgeon to shape the head to conform to the surface of target tissue. The tissue contact surface of ablation device 12 may be shaped or is shapeable to conform to the surface of the target tissue, for example, cardiac tissue. The suction head may comprise one or more suction ports, openings or elements 44 positioned on, along, within or adjacent the tissue contact surface. Suction openings 44 may communicate suction through the tissue contact surface to the atmosphere. The suction head may comprise one or more energy transfer elements positioned on, along, within or adjacent the tissue contact surface. Suction elements 44 are used to secure ablation device 12 to a target tissue surface thereby placing one or more energy transfer elements or sensors against tissue to be ablated or sensed. Target tissue may comprise a beating heart or a stopped heart. One or more suction elements 44 may be used to remove fluids.

Energy transfer elements transfer tissue ablation energy to target tissue. For example, energy transfer elements may be conductive elements 22 which may supply RF energy, microwave energy or ultrasound energy, as mentioned above, to for ablation of target tissue. Energy transfer elements may be, for example, laser elements for supplying laser light to ablate target tissue or they may be cryo elements for cryo-ablation of target tissue. Two or more energy transfer elements or conductive elements 22 of ablation device 12 may be arranged in a biopolar arrangement wherein at least one element 22 is used as a positive electrode and at least one element 22 is used as a negative electrode. One or more energy transfer elements or conductive elements 22 of ablation device 12 may be arranged in a monopolar arrangement wherein at least one element 22 is used as one electrode and an indifferent (non-ablating) electrode 23 is placed elsewhere on the patient's body such as the back, thigh or shoulder or another site other than the ablation site.

Energy transfer elements or conductive elements 22 may comprise one or more conductive materials or blends including titanium, titanium alloys, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, conductive polymers or plastics, or conductive ceramics. Energy transfer elements or conductive elements 22 may not be conductive but may serve as a conduit to deliver a conductive material such as a conductive fluid. Energy transfer elements or conductive elements 22 may be porous. For example, energy transfer elements or conductive elements 22 may comprise porous polymers, metals, or ceramics. Energy transfer elements or conductive elements 22 may be coated with non-stick coatings such as PTFE or other types of coatings as discussed herein. Energy transfer elements or conductive elements 22 may be flexible thereby allowing them to conform to the surface of target tissue. Energy transfer elements or conductive elements 22 may be malleable thereby allowing a surgeon to shape them to conform to the surface of target tissue.

Energy transfer elements or conductive elements 22 may comprise one or more metal conductors such as windings inside a polymer or a conductive mesh material. The energy transfer elements or conductive elements 22 may comprise tubes for delivering fluids. The tubes may comprise holes or slots. A polymer tube may be placed inside a metal tube to control fluid deliver through energy transfer elements or conductive elements 22. One or more of the energy transfer elements or conductive elements 22 may be used as nerve stimulation electrodes or as cardiac stimulation electrodes.

Energy transfer elements or conductive elements 22 may comprise needles designed to penetrate tissues such as fat and muscle. For example, energy transfer elements or conductive elements 22 may be designed to penetrate fat on the heart thereby allowing the energy transfer elements or conductive elements 22 to reach cardiac tissue. The needles may allow fluids such as conductive fluids, tissue ablation chemicals, drugs, and/or cells to pass through.

Ablation device 12 may comprise a surgeon-controlled switch 79. For example, a switch may be incorporated in or on ablation device 12 or any other location easily and quickly accessed by the surgeon for regulation of ablation device 12 by the surgeon. The switch may be, for example, a hand switch, a foot switch, or a voice-activated switch comprising voice-recognition technologies.

A visual and/or audible signal used to alert a surgeon to the completion or resumption of ablation may be incorporated into ablation device 12. For example, a beeping tone or flashing light that increases in frequency as the ablation period ends or begins may be used.

Ablation device 12 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. It is also contemplated that the ablation device 12 may be used in other ways, for example, in open-chest surgery on a heart in which the sternum is split and the rib cage opened with a retractor.

Figure 7:
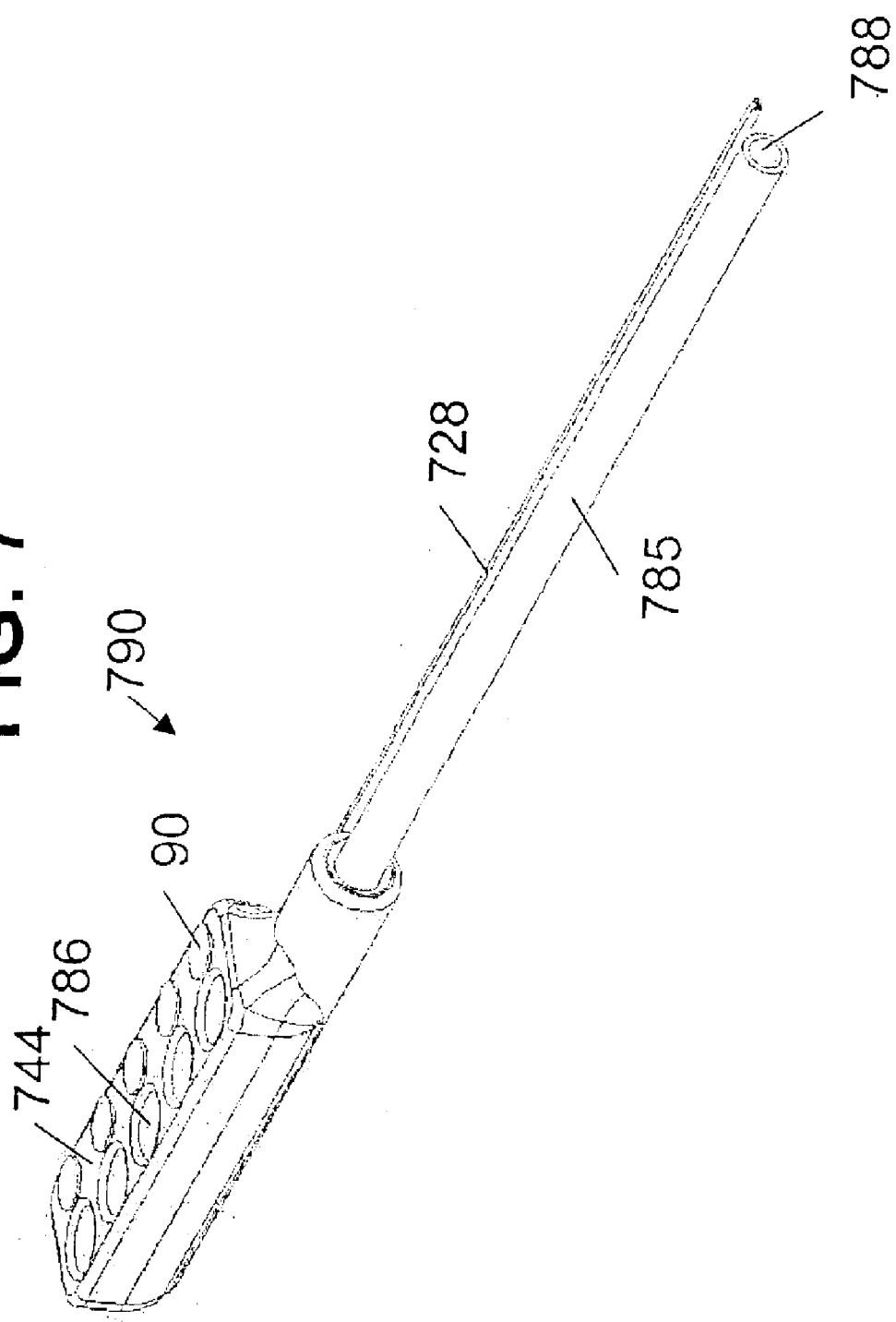
FIG. 7 illustrates an alternative embodiment of a sensor device for sensing in accordance with the present invention.

System 10 may also include a suction source (not shown) for providing suction to ablation device 12. Ablation device 12 may comprise one or more suction devices, elements or ports to better anchor ablation device 12 to tissue. Suction may also be used to anchor sensor 90 to a surface of tissue. FIG. 7 shows an alternative embodiment of sensor 90 wherein at least one sensor 90 is integrated into sensor device 790. In this embodiment, sensor device 790 may comprise one or more suction elements, openings, orficies, or ports 786 positioned or integrated within or along a tissue contact or support surface 744. Sensor device 790 may be powered by any suitable power source. For example, connection 728 may provide power to one or more sensor 90 from power source 30, generator 80, or an output device.

Support surface 744 may be attached to a flexible or rigid hose or tubing for supplying suction from a suitable suction source to the target tissue surface through suction ports 786 of sensor device 790. Support surface 744 may be attached to a maneuvering means for placing or positioning sensing elements against tissue. For example, sensor device 790 may comprise a shaft or handle 785 coupled to support surface 744. Handle 785 may comprise suction lumen 788 for communicating suction from a suitable suction source to the target tissue surface through suction ports 786 of sensor device 790. Suction conduit or lumen 788 may be connected to least one suction port 786 containing a suction opening. Suction ports 786 may be arranged in any suitable fashion, such as a row or circle. In addition, the specific number of ports and their position may vary. Sensor device 790 may be covered with a removable covering during insertion into a patient's body to prevent blood or tissue from clogging suction openings 786, although this is not necessary. Such coverings may include coverings of biocompatible material that would cover sensor device 790. Alternatively, coverings may be placed over ports 786, such as, for example, mesh coverings or ribbed coverings.

Each suction port or opening 786 may have a suction aperture coupling port 786 with conduit 788. Suction aperture may be located in the center or at a position slightly off-center of suction port 786. Suction aperture may be any shape including circular. The suction ports 786 may also be any suitable shape, for example circular, oval, rectangular, or triangular.

Preferably, each suction aperture would have a smaller diameter than the area of suction port 786. This creates a high resistance pathway between suction port 786 and suction conduit 788. Because of this, loss of a tissue-to-port seal in one suction port (and thus loss of fixation of the suction port to the tissue) should not cause a precipitous pressure drop in the remainder of the suction ports.

Suction may be provided to ablation device 12 and/or sensor device 790 by the standard suction available in the operating room. The suction source may be coupled to ablation device 12 and/or sensor device 790 with a buffer flask (not shown). Suction may be provided at a negative pressure of between 200–600 mm Hg with 400 mm Hg preferred. Alternatively, suction may be provided via a manual or electric pump, a syringe, a suction or squeeze bulb or other suction or vacuum producing means, device or system. Suction source 20 may comprise one or more vacuum regulators, valves, e.g., vacuum releasing valves, conduits, lines, tubes and/or hoses. The conduits, lines, tubes, or hoses may be flexible or rigid. For example, a flexible suction line may be used to communicate suction to ablation device 12 and/or sensor device 790, thereby allowing ablation device 12 and/or sensor device 790 to be easily manipulated by a surgeon. Another method that would allow the surgeon to easily manipulate ablation device 12 and/or sensor device 790 includes incorporation of suction source 20 into ablation device 12 and/or sensor device 790. For example, a small battery operated vacuum pump may be incorporated into ablation device 12 and/or sensor device 790.

Suction source 20 may be slaved to ablation device 12, generator 80 and/or sensor 90. For example, suction source 20 may be designed to automatically stop suction when ablation is stopped and to start suction when ablation is began. Suction source 20 may include a visual and/or audible signal used to alert a surgeon to any change suction. For example, a beeping tone or flashing light may be used to alert the surgeon when suction is present.

Figure 8:
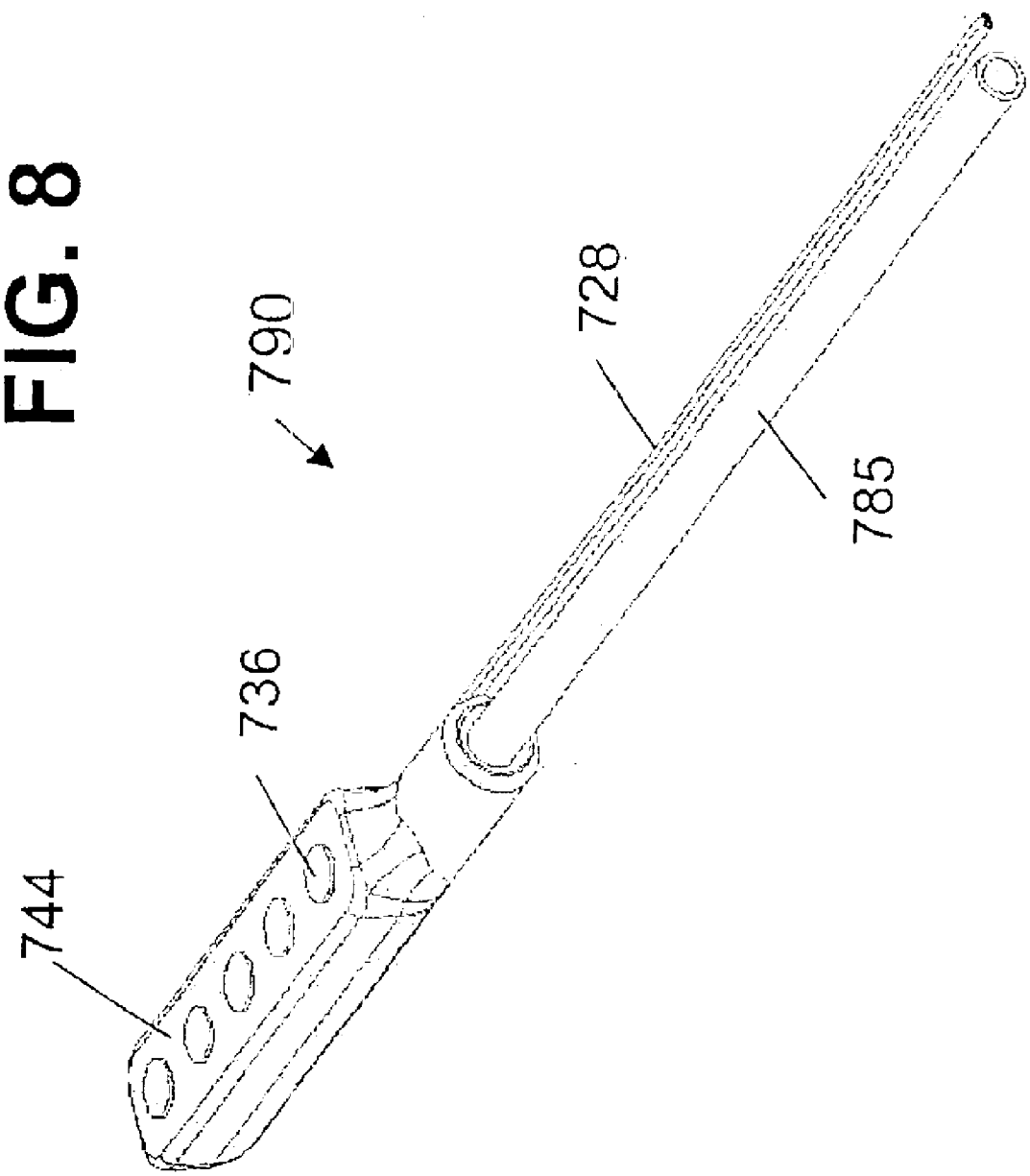
FIG. 8 illustrates an alternative embodiment of a sensor device for sensing in accordance with the present invention.

FIG. 8 shows an alternative embodiment of sensor device 790 comprising a plurality of temperature-sensing elements 736 aligned in a row on a support surface 744. Support surface 744 may be attached to handle 785. Handle 785 may be rigid or flexible. Handle 785 may comprise one or more hinges or joints (not shown) for maneuvering and placing sensor elements 736 against tissue. The hinges or joints of handle 785 may be actuated remotely, for example, from outside a patient's body. Handle 785 may be malleable or shapeable. Connection 728 may provide power to sensor device 790 from power source 30, generator 80, or an output device.

Sensor device 790 may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

Sensor device 790 may include or be operatively coupled with a surgeon-controlled switch. For example, a switch may be incorporated in or on sensor device 790 or any other location easily and quickly accessed by the surgeon for regulation of sensor 90 by the surgeon. The switch may be, for example, a hand switch, a foot switch, or a voice-activated switch comprising voice-recognition technologies.

Sensor device 790 may include, or may be coupled with a device that generates, a visual and/or audible signal used to alert a surgeon to any change, for example, in tissue temperature. For example, a beeping tone or flashing light may be used to alert the surgeon that a change has occurred in tissue temperature.

An output device (not shown) may receive and preferably interpret the signal from sensor 90. The signal from sensor 90 may preferably be amplified by a suitable amplifier before reaching the output device comprising a processor unit. The amplifier may be incorporated into the output device. Alternatively the amplifier may be incorporated into sensor 90, ablation device 12 or generator 80. Alternatively, the amplifier may be a separate device. The output device may be a device separate from ablation device 12, sensor 90, power source 30, irrigation source 40, or generator 80. The output device may be incorporated into ablation device 12, sensor 90, power source 30, irrigation source 40, or generator 80. The output device may control the power level from the power source 30 or generator 80. For example, a signal of a first intensity from sensor 90 may indicate that the power level from power source 30 should be lowered; a signal of a different intensity may indicate that the power source 30 should be turned off. Preferably, the output device may be configured so that it may automatically raise or lower the power from source 30 appropriately. Alternatively, the control of power source 30 based on output from the output device may be manual.

The output device may also be a visual display that indicates to the user that ablation energy should be halted. Such a display may be, for example, an indicator on a LCD or CRT monitor. By software control, the user may choose to display the information in a number of ways. The monitor may show the current temperature of each point of sensor contact. The monitor may also lock and display the maximum temperature achieved at each point of sensor contact. The monitor may also indicate when each point of contact has reached an appropriate combination of temperature and time to ensure cell death. One such appropriate combination may be 60° C. for 5 seconds. Another combination may be 55° C. for 20 seconds. Another combination may be 50° C. for 15 seconds. Temperature information may be displayed to the user in any other suitable manner, such as for example, displaying a virtual representation of sensor 90 and an ablation lesion on the monitor.

Alternatively, the monitor may display the voltage corresponding to the signal emitted from sensor 90. This signal corresponds in turn to the intensity of the temperature at the tissue site. Therefore a voltage level of 2 would indicate that the tissue was hotter than when the voltage level was 1. In this example, a user would monitor the voltage level and, if it exceeded a certain value, would turn off or adjust the power source 30.

The display of the output device may alternatively be located on sensor 90 or ablation device 12. An indicator, such as an LED light, may be permanently or removably incorporated into sensor 90 or ablation device 12. The indicator may receive a signal from sensor 90 indicating that the tissue had reached an appropriate temperature. In response, the indicator may turn on, change color, grow brighter or change in any suitable manner to indicate that the flow of power from source 30 should be modified or halted. The indicator may also be located on power source 30, on generator 80, on irrigation source 40, or may be located on another location visible to the user.

Alternatively, the output device may be an audio device that indicates to the user that ablation energy should be halted. Such an audio device may be, for example, a speaker that broadcasts a sound (for example, a beep) that increases in intensity, frequency or tone as the temperature sensed by sensor 90 increases. The user may adjust, for example, turn down or turn off power source 30 when the sound emitted reaches a given volume or level. In another embodiment, the audio device may also give an audible signal (such as the message "turn off power source"), for example, when the temperature sensed by sensor 90 reaches a certain level. Such an audio device may be located on the sensor 90 or ablation apparatus 12, on power source 30, on generator 80, or on irrigation source 40. The audio device may also be a separate device.

Figure 9:
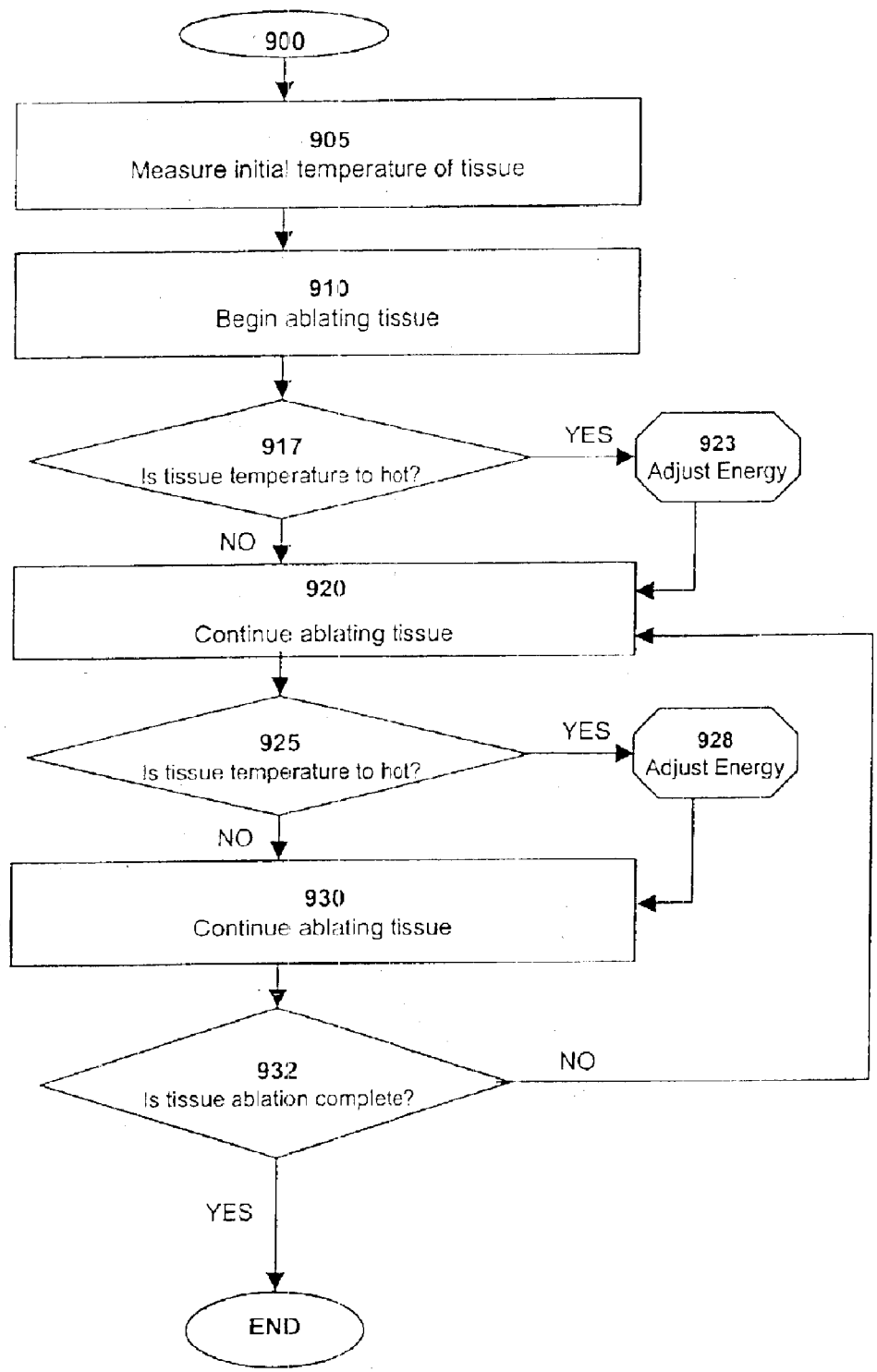
FIG. 9 shows a flow diagram of one embodiment of the present invention.

FIG. 9 shows a flow diagram of one embodiment of the present invention. The patient is prepared for an ablation procedure at 900. Once the patient is prepared, the initial state of tissue temperature is measured (Block 905). The initial state of tissue temperature is then used as a gauge to compare with the state of tissue temperature during the procedure. At this point, ablation of the target tissue is begun (Block 910). Tissue temperature is then monitored (Blocks 917 and 925). If the tissue temperature becomes to hot, the energy supplied to ablation apparatus 12 is modified or adjusted (Blocks 923 and 928).

Irrigation source 40, as discussed above, may be any suitable source of irrigation fluid. Irrigation source 40 may include a manual or electric pump, an infusion pump, a syringe pump, a syringe, or squeeze bulb or other fluid moving means, device or system. For example, a pump may be connected to power source 30 or it may have its own source of power. Irrigation source 40 may be powered by AC current, DC current, or it may be battery powered either by a disposable or re-chargeable battery. Irrigation source 40 may comprise one or more fluid regulators, e.g., to control flow rate, valves, fluid reservoirs, conduits, lines, tubes and/or hoses. The conduits, lines, tubes, or hoses may be flexible or rigid. For example, a flexible suction line may be used to communicate fluid to ablation device 12, thereby allowing ablation device 12 to be easily manipulated by a surgeon. Fluid reservoirs may be an IV bag or bottle, for example. It is preferred that the irrigation fluid be sterile.

Irrigation source 40 may be incorporated into ablation device 12, thereby delivering irrigation fluid at the ablation site. Irrigation source 40 may be slaved to ablation device 12, generator 80 and/or sensor 90. For example, irrigation source 40 may be designed to automatically stop or start the delivery of irrigation fluid during ablation of tissue. Irrigation source 40 may be slaved to a robotic system or a robotic system may be slaved to irrigation source 40. Irrigation source 40 may comprise a surgeon-controlled switch. For example, a switch may be incorporated in or on irrigation source 40 or any other location easily and quickly accessed by the surgeon for regulation of irrigation fluid delivery by the surgeon. The switch may be, for example, a hand switch, a foot switch, or a voice-activated switch comprising voice-recognition technologies. Irrigation source 40 may include a visual and/or audible signal used to alert a surgeon to any change in the delivery of irrigation fluid. For example, a beeping tone or flashing light may be used to alert the surgeon that a change has occurred in the delivery of irrigation fluid.

As discussed earlier, an irrigation fluid may include saline, e.g., normal, hypotonic or hypertonic saline, Ringer's solution, ionic contrast, blood, or other energy-conducting liquids. An ionic irrigation fluid electrically couples the one or more electrodes of ablation device 12 to the tissue to be ablated thereby lowering the impedance at the ablation site. An ionic irrigating fluid may create a larger effective electrode surface. An irrigating fluid may cool the surface of the tissue thereby preventing the over heating or cooking of tissue which can cause popping, desiccation, and charring of tissue. A hypotonic irrigating fluid may be used to electrically insulate a region of tissue thereby preventing ablation of tissue by an electrical means.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered before, with or after the delivery of the irrigating fluid. Biological agents may be found in nature (naturally occurring) or may be chemically synthesized. Cells and-cell components, e.g., mammalian cells, may be delivered before, with or after the delivery of the irrigating fluid.

Generator 80 may comprise a control unit and power source 30. As discussed earlier, ablation device 12 may be permanently or removably attached to a source of energy such as electrical, radiofrequency (RF), laser, thermal, microwave or ultrasound or any other appropriate type of energy that may be used to ablate tissue. Generator 80 may be powered by AC current, DC current or it may be battery powered either by a disposable or re-chargeable battery. Generator 80 may be used to coordinate the various elements of system 10. For example, generator 80 may be configured to synchronize activation and deactivation of suction source 20 with ablation.

Generator 80 may incorporate a controller as described above or any suitable processor. For example, the processor may process sensed information from sensor 90. The controller may store and/or process such information before, during and/or after an ablation procedure. For example, the patient's tissue temperature may be sensed, stored and processed prior to and during the ablation procedure.

Generator 80 may be used to control the power levels of ablation device 12. Generator 80 may also gather and process information from sensor 90. This information may be used to adjust power levels and ablation times. Generator 80 may incorporate one or more switches 79 to facilitate regulation of the various system components by the surgeon. One example of such a switch is a foot pedal. The switch may also be, for example, a hand switch, or a voice-activated switch comprising voice-recognition technologies. The switch may be incorporated in or on one of the surgeon's instruments, such as surgical site retractor, e.g., a sternal or rib retractor, or ablation device 12, or any other location easily and quickly accessed by the surgeon. Generator 80 may also include a display. Generator 80 may also include other means of indicating the status of various components to the surgeon such as a numerical display, gauges, a monitor display or audio feedback.

Generator 80 may also incorporate a cardiac stimulator and/or cardiac monitor. For example, electrodes used to stimulate or monitor the heart may or may not be incorporated into ablation device 12. Generator 80 may comprise a surgeon-controlled switch for cardiac stimulation or monitoring, as discussed earlier. For example, a switch may be incorporated in or on generator 80 or any other location easily and quickly accessed by the surgeon for regulation of generator 80 by the surgeon. The switch may be, for example, a hand switch, a foot switch, or a voice-activated switch comprising voice-recognition technologies.

A visual and/or audible signal used to alert a surgeon to the completion or resumption of ablation, suction, sensing, monitoring, stimulation and/or delivery of irrigation fluid, drugs and/or cells may be incorporated into generator 80. For example, a beeping tone or flashing light that increases in frequency as the ablation period ends or begins may be used.

System 10, ablation device 12, and/or sensor device 790 may comprise one or more temperature-sensitive elements 36, such as a thermocouple as discussed above, to allow a surgeon to monitor temperature changes of a patient's tissue. For example, FIGS. 7 and 8 show two different embodiments of sensor device 790 comprising a plurality of temperature-sensitive elements 736 positioned along support surface 744. Alternatively, system 10, ablation device 12, sensor device 790 and/or sensor 90 may sense and/or monitor voltage, amperage, wattage and/or impedance.

Alternatively, sensor 90 may be any suitable blood gas sensor for measuring the concentration or saturation of a gas in the blood stream. For example, sensor 90 may be a sensor for measuring the concentration or saturation of oxygen or carbon dioxide in the blood. Alternatively, sensor 90 may be any suitable sensor for measuring blood pressure or flow, for example a Doppler ultrasound sensor system, or a sensor for measuring hematocrit (HCT) levels.

Alternatively sensor 90 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Sensor 90 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

Sensor 90 may be used to detect naturally detectable properties representative of one or more characteristics, e.g., chemical, physical or physiological, of a patient's bodily tissues or fluids. For example, naturally detectable properties of patient's bodily tissues or fluids may include pH, fluid flow, electrical current, impedance, temperature, pressure, components of metabolic processes, chemical concentrations, for example, the absence or presence of specific peptides, proteins, enzymes, gases, ions, etc.

Sensor 90 may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; visible light sensors; IR light sensors; radiation sensors; flow sensors; temperature sensors; or any other appropriate or suitable sensor.

Sensor 90 may be incorporated into ablation device 12, for example, as discussed above, or sensor 90 may be incorporated into sensor device 790, for example, as discussed above. Sensor 90 may be placed or used at a location differing from the location of ablation device 12. For example, sensor 90 may be placed in contact with the inside surface of a patient's heart while ablation device 12 is placed or used on the outside surface of the patient's heart.

Ablation device 12 and/or generator 80 may be slaved to sensor 90. For example, ablation device 12 and/or generator 80 may be designed to automatically stop ablation if sensor 90 measures a predetermined sensor value, e.g., a particular temperature value. In one embodiment of the invention, if sensor 90 of the present invention indicates that ablated tissue has reached a particular temperature, ablation is stopped automatically, thereby preventing charring of the tissue.

Sensor 90 may include a visual and/or audible signal used to alert a surgeon to any change in the one or more characteristics the sensor is monitoring. For example, a beeping tone or flashing light that increases in frequency as tissue temperature rises may be used to alert the surgeon.

Ablation device 12, suction source 20, irrigation source 40, generator 80, and/or sensor 90 may be, slaved to a robotic system or a robotic system may be slaved to ablation device 12, suction source 20, irrigation source 40, generator 80, and/or sensor 90. Computer- and voice-controlled robotic systems that position and maneuver endoscopes and/or other surgical instruments for performing microsurgical procedures through small incisions may be used by the surgeon to perform precise and delicate maneuvers. These robotic systems may allow the surgeon to perform a variety of microsurgical procedures including tissue ablation. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

One or more of a variety of pharmacological agents or drugs may be delivered or administered to an ablation patient, for a variety of functions and purposes as described below, prior to an ablation procedure, intermittently during an ablation procedure, continuously during an ablation procedure and/or following an ablation procedure. For example, one or more of a variety of pharmacological agents or drugs, as discussed below, may be delivered before, with or after the delivery of the irrigating fluid, as discussed earlier.

Drugs, drug formulations or compositions suitable for administration to an ablation patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, system 10 may include a drug delivery device (not shown). The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes. Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into ablation device 12, thereby delivering drugs at or adjacent the ablation site or the drug delivery device may be placed or used at a location differing from the location of ablation device 12. For example, a drug delivery device may be placed in contact with the inside surface of a patient's heart while ablation device 12 is placed or used on the outside surface of the patient's heart.

The drug delivery device may be slaved to ablation device 12, generator 80 and/or sensor 90. For example, a drug delivery device may be designed to automatically stop or start the delivery of drugs during ablation of tissue. The drug delivery device may be slaved to a robotic system or a robotic system may be slaved to the drug delivery device.

The drug delivery device may comprise a surgeon controlled switch. For example, a switch may be incorporated in or on the drug delivery device or any other location easily and quickly accessed by the surgeon for regulation of drug delivery by the surgeon. The switch may be, for example, a hand switch, a foot switch, or a voice-activated switch comprising voice-recognition technologies.

The drug delivery device may include a visual and/or audible signal used to alert a surgeon to any change in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid-sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

One or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytbkine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered or administered to an ablation patient prior to an ablation procedure, intermittently during an ablation procedure, continuously during an ablation procedure and/or following an ablation procedure. Biological agents may be found in nature (naturally occurring) or may be chemically synthesized.

The ablation procedure may be non-invasive, minimally invasive and/or invasive. The ablation procedure may entail a port-access approach, a partially or totally endoscopic approach, a sternotomy approach or a thoracotomy approach. The ablation procedure may include the use of various mechanical stabilization devices or techniques as well as various robotic or imaging systems. For example, mechanical stabilization and manipulation devices are described in U.S. Pat. Nos. 5,836,311; 5,927,284 and 6,015,378, and co-assigned U.S. patent applications Ser. No. 09/396,047, filed Sept. 15, 1999, Ser. No. 09/559,785, filed Apr. 27, 2000, and Ser. No. 09/678,203, filed Oct. 2, 2000; and European Patent Publication No. EP 0 993 806. These patents and applications are assigned to Medtronic, Inc. and are incorporated herein by reference.

In one method of the present invention, the heart may be temporarily slowed or intermittently stopped for short periods of time to permit the surgeon to accomplish a required surgical task and yet still allow the heart itself to supply blood circulation to the body. For example, stimulation of the vagus nerve in order to temporarily and intermittently slow or stop the heart is described in U.S. Pat. No. 6,006,134 entitled "Method and Device for Electronically Controlling the Beating of a Heart Using Venous Electrical Stimulation of Nerve Fibers", Dec. 21, 1999, to Hill and Junkman. This patent is assigned to Medtronic, Inc. and is incorporated herein by reference.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A system for suction assisted ablation for creating a tissue ablation site, the system comprising:
   a tissue contact surface;
   a plurality of suction ports positioned substantially linearly along the tissue contact surface and capable of drawing a portion of tissue at least partially within the suction ports upon application of suction;
   a suction conduit for providing suction from a suction source to the suction ports, the suction conduit operatively connected with the suction ports;
   a first elongated energy transfer element positioned along the tissue contact surface and extending adjacent a first side of each of the suction ports;
   a second elongated energy transfer element positioned along the tissue contact surface and extending adjacent a second side of each of the suction ports, said first and second energy transfer elements capable of forming a linear transmural lesion in the portion of tissue drawn within the suction ports by application of energy via the first and second energy transfer elements;
   a sensor sensing a parameter or characteristic relating to the tissue ablation site positioned along the tissue contact surface; and
   means for automatically stopping ablation in response to a signal from the sensor.

2. The system of claim 1 further comprising a maneuvering apparatus operatively connected with the tissue contact surface.

3. The system of claim 2 wherein the maneuvering apparatus includes at least one pull wire.

4. The system of claim 2 wherein the maneuvering apparatus includes a handle.

5. The system of claim 4 wherein the handle comprises one or more hinges or joints.

6. The system of claim 5 wherein the one or more hinges or joints are actuated remotely.

7. The system of claim 4 wherein the handle is shapeable.

8. The system of claim 1 wherein the tissue contact surface is flexible.

9. The system of claim 1 wherein the tissue contact surface is shaped to conform to the tissue ablation site.

10. The system of claim 1 further comprising a suction source operatively connected to the suction conduit.

11. The system of claim 10 further comprising one or more surgeon-controlled switches operatively connected to the suction source.

12. The system of claim 1 wherein the system further comprises means for varying energy supplied to the energy transfer elements in response to the sensed parameter or characteristic of the tissue ablation site.

13. The system of claim 1 wherein the parameter or characteristic is temperature.

14. The system of claim 1 wherein the parameter or characteristic is impedance.

15. The system of claim 1 wherein the parameter or characteristic is pressure.

16. The device of claim 1 wherein the system further comprises an output device for alerting or informing a practitioner regarding the parameter or characteristic of the tissue ablation site sensed by the sensor.

17. The system of claim 1 further comprising an electrical source operatively coupled to the energy transfer elements.

18. The system of claim 1 further comprising an RF energy source operatively coupled to the energy transfer elements.

19. The system of claim 1 further comprising a laser energy source operatively coupled to the energy transfer elements.

20. The system of claim 1 further comprising a thermal energy source operatively coupled to the energy transfer elements.

21. The system of claim 1 further comprising an ultrasound energy source operatively coupled to the energy transfer elements.

22. The system of claim 1 further comprising a microwave energy source operatively coupled to the energy transfer elements.

23. A system for suction assisted ablation for creating a tissue ablation site, the system comprising:
   a tissue contact surface;
   a plurality of suction ports positioned generally linearly along the tissue contact surface and capable of drawing a portion of tissue at least partially within the suction ports upon application of suction;
   a suction conduit for providing suction from a suction source to the suction port, the suction conduit operatively connected with the suction ports;
   a first elongated energy transfer element positioned along the tissue contact surface and extending adjacent a first side of each of the suction ports;
   a second elongated energy transfer element positioned alone the tissue contact surface and extending adjacent a second side of each of the suction ports, said first and second energy transfer elements capable of forming a substantially linear transmural lesion in the portion of tissue drawn within the suction ports by application of energy via the first and second energy transfer elements;
   a sensor sensing a parameter or characteristic relating to the tissue ablation site positioned along the tissue contact surface; and
   means for varying suction communicated to the suction ports in response to the sensed parameter or characteristic.

24. The system of claim 23 further comprising a maneuvering apparatus operatively connected with the tissue contact surface.

25. The system of claim 24 wherein the maneuvering apparatus includes a handle.

26. The system of claim 23 wherein the tissue contact surface is flexible.

27. The system of claim 23 wherein the tissue contact surface is shaped to conform to the tissue ablation site.

28. The system of claim 23 further comprising one or more surgeon-controlled switches operatively connected to the suction source.

29. The system of claim 23 wherein the parameter or characteristic is temperature.

30. The system of claim 23 wherein the parameter or characteristic is impedance.

31. The system of claim 23 wherein the parameter or characteristic is pressure.

32. The system of claim 23 wherein the system further comprises an output device for alerting or informing a practitioner regarding the parameter or characteristic of the tissue ablation site sensed by the sensor.

33. The system of claim 23 further comprising an electrical source operatively coupled to the energy transfer elements.

34. The system of claim 23 further comprising an RF energy source operatively coupled to the energy transfer elements.

35. The system of claim 23 further comprising a laser energy source operatively coupled to the energy transfer elements.

36. The system of claim 23 further comprising a thermal energy source operatively coupled to the energy transfer elements.

37. The system of claim 23 further comprising an ultrasound energy source operatively coupled to the energy transfer elements.

38. The system of claim 23 further comprising a microwave energy source operatively coupled to the energy transfer elements.

39. A system for suction assisted ablation for creating a tissue ablation site, the system comprising:

a tissue contact surface;

a plurality of suction ports positioned substantially linearly along the tissue contact surface and capable of drawing a portion of tissue at least partially within the suction ports upon application of suction;

a suction conduit for providing suction from a suction source to the suction port, the suction conduit operatively connected with the suction ports;

a first elongated energy transfer element positioned along the tissue contact surface and extending adjacent a first side of each of the suction ports;

a second elongated energy transfer element positioned alone the tissue contact surface and extending adjacent a second side of each of the suction ports, said first and second energy transfer elements capable of forming a substantially linear transmural lesion in the portion of tissue drawn within the suction ports by application of energy via the first and second energy transfer elements;

a sensor sensing a parameter or characteristic relating to the tissue ablation site positioned along the tissue contact surface;

an irrigation fluid conduit for providing irrigation fluid from an irrigation source to the tissue ablation site; and means for varying irrigation fluid supplied to the irrigation conduit in response to the sensed parameter or characteristic.

40. The system of claim 39 further comprising a maneuvering apparatus operatively connected with the tissue contact surface.

41. The system of claim 40 wherein the maneuvering apparatus includes a handle.

42. The system of claim 39 wherein the tissue contact surface is flexible.

43. The system of claim 39 wherein the tissue contact surface is shaped to conform to the tissue ablation site.

44. The system of claim 39 further comprising one or more surgeon-controlled switches operatively connected to the irrigation source.

45. The system of claim 39 wherein the parameter or characteristic is temperature.

46. The system of claim 39 wherein the parameter or characteristic is impedance.

47. The system of claim 39 wherein the parameter or characteristic is pressure.

48. The system of claim 39 wherein the system further comprises an output device for alerting or informing a practitioner regarding the parameter or characteristic of the tissue ablation site sensed by the sensor.

49. The system of claim 39 further comprising an electrical source operatively coupled to the energy transfer elements.

50. The system of claim 39 further comprising an RF energy source operatively coupled to the energy transfer elements.

51. The system of claim 39 further comprising a laser energy source operatively coupled to the energy transfer elements.

52. The system of claim 39 further comprising a thermal energy source operatively coupled to the energy transfer elements.

53. The system of claim 39 further comprising an ultrasound energy source operatively coupled to the energy transfer elements.

54. The system of claim 39 further comprising a microwave energy source operatively coupled to the energy transfer elements.

55. A system for suction assisted ablation for creating a tissue ablation site, the system comprising:

a tissue contact surface;

a plurality of suction ports positioned generally linearly along the tissue contact surface and capable of drawing a portion of tissue at least partially within the suction ports upon application of suction;

a suction conduit for providing suction from a suction source to the suction ports, the suction conduit operatively connected with the suction ports;

a first elongated energy transfer element positioned along the tissue contact surface and extending adjacent a first side of each of the suction ports; and a second elongated energy transfer element positioned along the tissue contact surface and extending adjacent a second side of each of the suction ports, said first and second energy transfer elements capable of forming a generally linear transmural lesion in the portion of tissue drawn within the suction ports by application of energy via the first and second energy transfer elements.

56. The system of claim 55 further comprising a maneuvering apparatus operatively connected with the tissue contact surface.

57. The system of claim 56 wherein the maneuvering apparatus includes at least one pull wire.

58. The system of claim 56 wherein the maneuvering apparatus includes a handle.

59. The system of claim 58 wherein the handle comprises one or more hinges or joints.

60. The system of claim 59 wherein the one or more hinges or joints are actuated remotely.

61. The system of claim 59 wherein the handle is shapeable.

62. The system of claim 55 wherein the tissue contact surface is flexible.

63. The system of claim 55 wherein the tissue contact surface is shaped to conform to the tissue ablation site.

64. The system of claim 55 further comprising a suction source operatively connected to the suction conduit.

65. The system of claim 64 further comprising one or more surgeon-controlled switches operatively connected to the suction source.

66. The system of claim 55 further comprising an electrical source operatively coupled to the energy transfer elements.

67. The system of claim 55 further comprising an RF energy source operatively coupled to the energy transfer elements.

68. The system of claim 55 further comprising a laser energy source operatively coupled to the energy transfer elements.

69. The system of claim 55 further comprising a thermal energy source operatively coupled to the energy transfer elements.

70. The system of claim 55 further comprising an ultrasound energy source operatively coupled to the energy transfer elements.

71. Th system of claim 55 further comprising a microwave energy source operatively coupled to the energy transfer elements.

* * * * *